United States Patent
Jorkama

(10) Patent No.: US 7,162,932 B2
(45) Date of Patent: Jan. 16, 2007

(54) METHOD FOR DETERMINING THE MODULUS OF ELASTICITY OF PAPER

(75) Inventor: Marko Jorkama, Järvenpää (FI)

(73) Assignee: Metso Paper, Inc., Helsinki (FI)

( * ) Notice: Subject to any disclaimer, the term of this patent is extended or adjusted under 35 U.S.C. 154(b) by 0 days.

(21) Appl. No.: 10/532,148

(22) PCT Filed: Oct. 22, 2003

(86) PCT No.: PCT/FI03/00784

§ 371 (c)(1),
(2), (4) Date: May 20, 2005

(87) PCT Pub. No.: WO2004/038384

PCT Pub. Date: May 6, 2004

(65) Prior Publication Data

US 2006/0037389 A1   Feb. 23, 2006

(30) Foreign Application Priority Data

Oct. 24, 2002   (FI)   ................................. 20021902

(51) Int. Cl.
*G01L 1/04* (2006.01)
*G01L 5/04* (2006.01)

(52) U.S. Cl. ........................ 73/862.451; 73/159; 73/81; 73/83; 242/534

(58) Field of Classification Search ................... 73/159, 73/862.451, 81, 83; 242/534
See application file for complete search history.

(56) References Cited

U.S. PATENT DOCUMENTS

| | | | |
|---|---|---|---|
| 3,194,061 A * | 7/1965 | Sorenson et al. | ............... 73/81 |
| 3,718,037 A * | 2/1973 | Stringer et al. | ........ 73/862.454 |
| 3,822,588 A * | 7/1974 | Knight et al. | ................... 73/81 |
| 4,535,950 A | 8/1985 | Lisnyansky | |
| 4,676,094 A | 6/1987 | Hoffmann et al. | |
| 4,864,851 A | 9/1989 | Haughton | |
| 5,282,382 A | 2/1994 | Fiore et al. | |
| 5,297,062 A | 3/1994 | Cresson et al. | |
| 5,308,010 A * | 5/1994 | Hakiel | ......................... 242/534 |
| 5,402,673 A * | 4/1995 | Weinert et al. | ................. 73/82 |
| 5,535,627 A | 7/1996 | Swanson et al. | |
| 5,923,415 A * | 7/1999 | Sakata et al. | .............. 356/73.1 |
| 6,036,137 A | 3/2000 | Myren | |
| 6,363,297 B1 * | 3/2002 | Wienholt et al. | ........... 700/126 |
| 6,517,679 B1 * | 2/2003 | Mustonen et al. | .......... 162/198 |

(Continued)

FOREIGN PATENT DOCUMENTS

FI   840380   7/1988

(Continued)

OTHER PUBLICATIONS

International Preliminary Examination Report issued in PCT/FI02/00336.

(Continued)

*Primary Examiner*—Hezron Williams
*Assistant Examiner*—Samir M. Shah
(74) *Attorney, Agent, or Firm*—Stiennon & Stiennon

(57) ABSTRACT

In a method for determining the radial modulus of elasticity of paper or a corresponding web-like material that can be reeled or wound on a reel, the connection between the force and deflection of a material arranged in layers is measured. The measurements of force and deflection necessary for calculating the radial modulus of elasticity are performed on a reel of paper or corresponding material outside the reeling or winding position by loading the reel with a press member.

14 Claims, 4 Drawing Sheets

U.S. PATENT DOCUMENTS

2004/0163457 A1* 8/2004 Jorkama .................... 73/159

FOREIGN PATENT DOCUMENTS

| WO | WO 97/24595 A1 | 7/1997 |
| WO | WO 99/44058 A1 | 2/1999 |
| WO | WO99/44058 | * 9/1999 |
| WO | WO99/50719 | * 10/1999 |
| WO | WO 02/086456 A1 | 10/2002 |
| WO | WO 2004/038384 A1 | 5/2004 |

OTHER PUBLICATIONS

International Search Report tissued in PCT/FI02/00336.
"The Mechanics of Winding", D. Roisum, Tappi Press 1994, p. 62.
International Search Report issued in PCT/FI03/00784.

* cited by examiner

METHOD FOR DETERMINING THE MODULUS OF ELASTICITY OF PAPER

CROSS REFERENCES TO RELATED APPLICATIONS

This application is a U.S. national stage application of international App. No. PCT/FI2003/000784, filed Oct. 22, 2003, the disclosure of which is incorporated by reference herein. This application claims priority on Finnish App. No. 20021902, filed Oct. 24, 2002.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The present invention relates to a method for determining the radial modulus of elasticity of paper or a corresponding web-like material that can be reeled or wound on a reel. In said method the connection between the force and deflection of a material arranged in superimposed layers is measured.

A known method for measuring the radial modulus of elasticity of paper is a measurement conducted in a laboratory, which is disclosed for example in the publication by D. Roisum: The Mechanics of Winding, Tappi Press 1994, p. 62. The measurement is conducted in such a manner that a stack of paper sheets is pressed between two planes. As a result of the measurement a curve is attained, which represents the pressing force as a function of the height of the stack. The stress is obtained by dividing the force by the measurement area. The strain of the paper stack, which in this case is, in fact, compression, is obtained by dividing the change in the height by the original height of the stack. The paper stack is loaded until it reaches such stress which is substantially the same as the maximum stress that is assumed to be effective inside the reel. The loading of the paper stack is conducted several times in succession. The radial modulus of elasticity is the slope of the tangent of the stress-strain curve.

It is a problem of the laboratory measurement that it is conducted with a delay, in other words reactions to problems in the production occur slowly. The shape of the paper stack does not entirely correspond to the shape of the reel in the production machine. Furthermore, it is necessary to use a paper stack, wherein it is somewhat difficult to prepare a sample for the measurement. In this measurement it is, however, necessary to use a paper stack, because it is very difficult to measure single sheets and it may cause inaccurate results.

SUMMARY OF THE INVENTION

By means of the method according to the invention it is possible to eliminate or reduce the above-mentioned problems. The method according to the invention is characterized in that the measurements of force and deflection that are necessary in the determination of the radial modulus of elasticity are performed on a paper reel outside the reeling or winding position. The term reeling or winding position refers to the position in which the reel is located when material in the form of a continuous web is reeled or wound thereon.

The advantages of the method according to the invention are that the measurement of force and deflection can be performed on the reel, wherein the shape of the surface to be measured is correct. By means of the measurement, information is obtained which indicates how the reeling or winding should be conducted, for example which web tension should be utilized at a given time, in other words, the measurement results can be applied in theoretical winding models. Because the measurements are made on the finished reel, it is possible to rapidly react to errors in the reeling or winding. Inaccurately reeled or wound material can be reeled again or rejected. The method according to the invention can be applied after the reeling or winding position of reel-ups or winders of various types, such as center winders or carrier drum winders when the reel has been transferred to a special measurement position. The method can also be applied in a corresponding manner in continuously operated reel-ups.

When the aim is to use theoretical winding models to attain winding parameter recipes, it is necessary to know the constitutive behavior of the paper reel, i.e. the connection between the stress and strain of the paper reel. When an elastic orthotropic plane model is used, four variables are necessary for describing this connection, of which variables the radial modulus of elasticity is dependent on the pressure inside the reel and the other three variables are typically assumed to be constant. A method has now been developed for estimation of the radial modulus of elasticity, which method will be described hereinbelow.

When the method according to the invention is used, the measurements of force and deflection necessary in the calculation of the radial modulus of elasticity of paper or a corresponding material are conducted outside the reeling or winding position of paper or a corresponding material, in other words the reel is transferred from the reeling or winding position to a special measurement position. In the measurement a stationary (non-rotating) paper reel or the like is loaded with forces of different magnitude in the direction of the radius of the paper reel, and deflections corresponding to the forces are registered. In this application, the term deflection refers to the compression of layered paper or corresponding material on a reel in the direction of the radius of the reel when the reel is loaded with a force in the direction of the reel radius. The compression can be measured either directly from the movement of the press member in the radial direction of the reel, or indirectly from the extent of the contact area in the loading (the extent of the contact area in the direction of the periphery of the reel correlates with the deflection).

The measurement is conducted when the paper reel or the like is positioned in a measurement station which comprises means for producing and registering the deflection, and means for registering the force corresponding to the deflection. The measurement is conducted after the paper reel is finished, the reel is stopped and transferred thereafter to the measurement station. The reel is loaded with a known force and at the same time the deflection of the reel is measured. The member loading the reel in the measurement station can be a press member pressing the surface of the reel by means of a pivotal movement or linear movement. The measurement of the deflection can be conducted for example by measuring this movement, or the deflection-dependent extent of the contact area between the straight surface of the loading member and the surface of the paper reel in the loading situation. The force can be measured by means of a sensor placed in the press member, or on the basis of the force required by the loading movement. On the basis of the measurement result a curve is obtained showing the deflection in the direction of the radius of the reel as a function of the force loading the reel.

The deflections are determined using the same press member with different force values, wherein several pairs of measurement results (measurement points) of force and deflection are obtained. Their number is so large that it is possible to obtain a reliable force-deflection curve by means of them. In practice, it is possible to increase the force constantly, and measure the forces and the corresponding deflection at sufficiently short intervals or constantly, when the press member is pressed constantly towards the central axis of the reel in the direction of the radius.

The tangential modulus of elasticity of paper or corresponding web-like material to be reeled or wound, obtained as a measurement result either as a laboratory measurement or in the production machine, is placed in the theoretical loading model of the paper reel. Elastic parameters used as initial guesses are also necessary in the theoretical loading model. On the basis of the theoretical loading model another curve is obtained describing the deflection in the direction of the radius of the reel as a function of the force loading the reel.

The theoretical loading model of the paper reel can be for example a model utilizing FEM (finite element model) calculation. FEM calculation is known as such and therefore it will not be described in more detail. Generally, it can be said that the FEM calculation is utilized when the use of exact mathematical formulas is difficult for example due to their complex nature.

The curve obtained on the basis of the measurement results and the curve obtained on the basis of the theoretical loading model are compared to each other. If they match, the initial guess of the elastic parameters is correct. If the curves do not match, new values are given for the elastic parameters, and this process continues until the curve obtained by means of the theoretical loading model corresponds to the measurement results. The radial modulus of elasticity becomes entirely known for example from the elastic parameters that have been initially included in the calculation as guesses. On the basis of the obtained result it is possible to estimate the radial modulus of elasticity. In the estimation it is possible to use for example the least squares method in which a minimum of the square of the difference of the calculated and measured values is sought.

In the following, the invention will be described by means of drawings.

DESCRIPTION OF THE PREFERRED EMBODIMENTS

Figure 1:
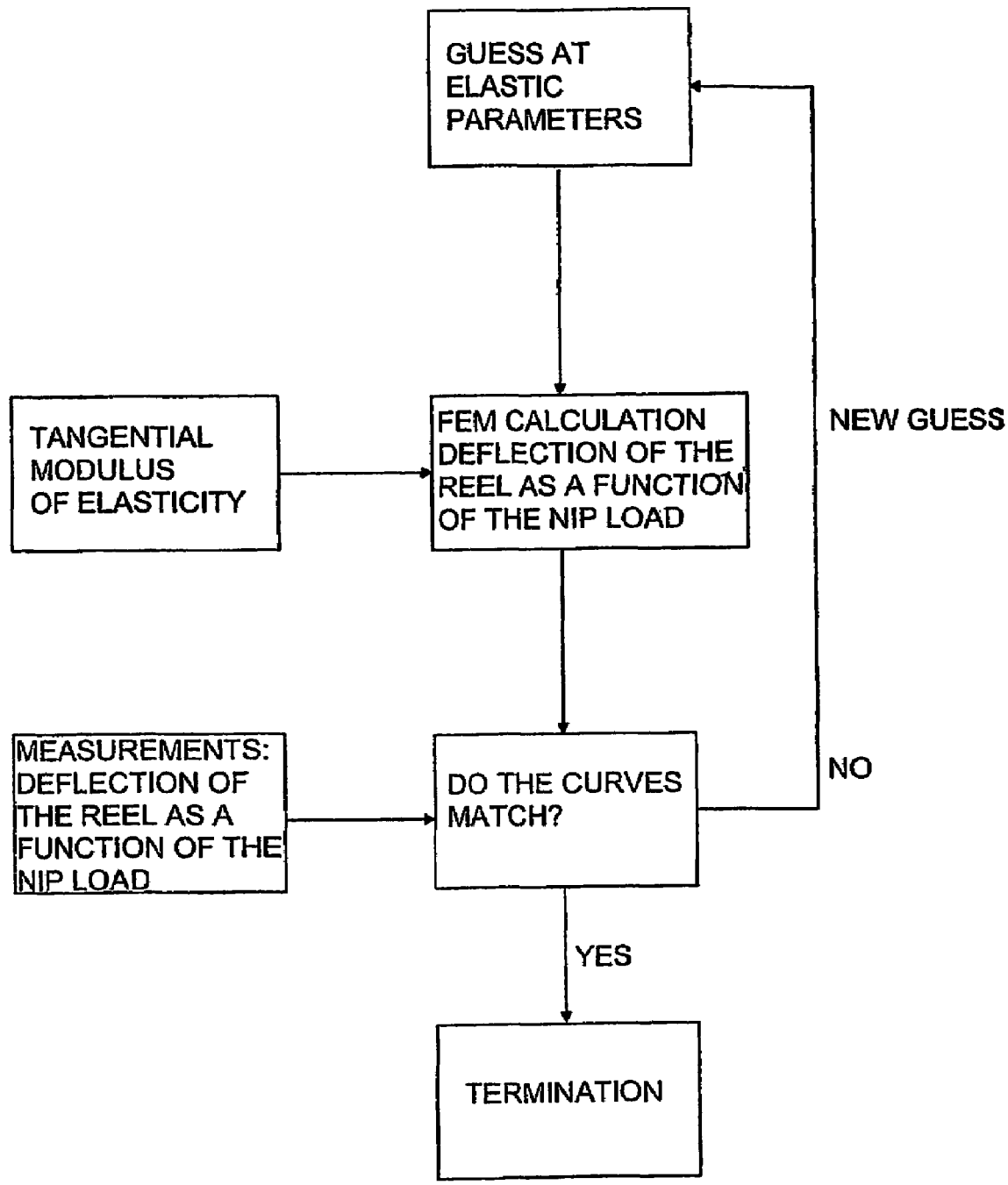
FIG. 1 shows the method according to the invention in a block diagram.

FIG. 1 shows the method according to the invention for measuring the radial modulus of elasticity of paper in a block diagram. To calculate the radial modulus of elasticity, an initial guess of the elastic parameters and a tangential modulus of elasticity measured from the paper are necessary.

The radial modulus of elasticity can be represented with the formula $E_r = E_r(\sigma_r)$, i.e. $E_r$ depends on the radial stress $\sigma_r$. This dependency can be described with a $1_{st}$ to $3_{rd}$ order polynomial. Elastic parameters which are required as initial guesses can be for example the coefficients of this polynomial.

The tangential modulus of elasticity can be measured by means of laboratory measurement, or it can be measured in the production machine. When the elastic parameters given as an initial guess are placed in the theoretical reeling model, and a curve of the compression of the reel as a function of the nip load is obtained as a result of the FEM calculation, the obtained curve is compared with the curve representing the deflection of the reel as a function of the nip load, obtained from the production machine as a measurement result. If the curves match, the initial guess is correct. If they do not match, new values are given for the elastic parameters and the comparison of the curves continues.

Figure 2:
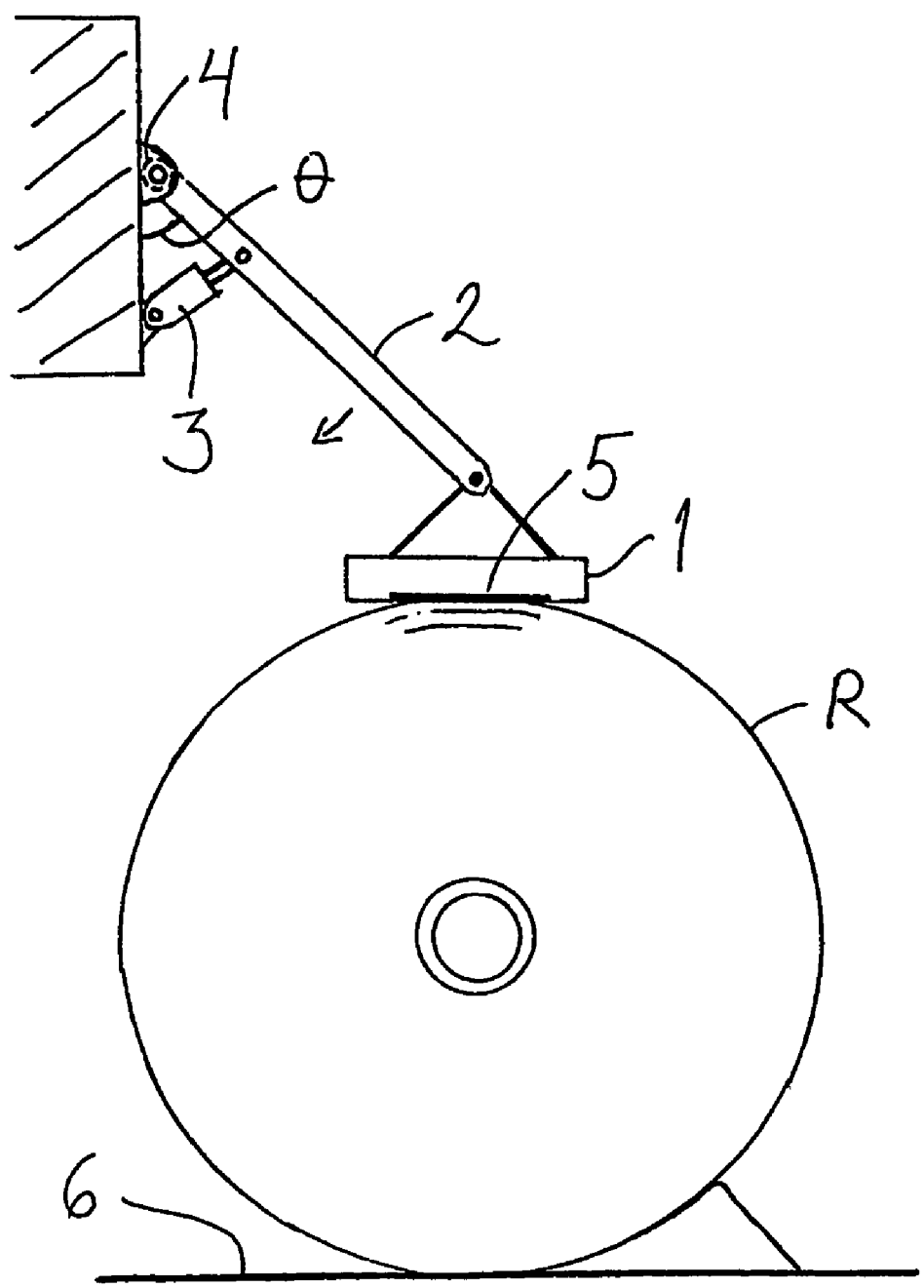
FIGS. 2 and 3 show, in side-views of the reel, some measurement stations in which it is possible to carry out the method according to the invention.

FIG. 2 illustrates the measurement performed on a paper roll in a position after a slitter winder. The measurement is conducted in the measurement station, for example after a WinBelt® winder or a WinRoll™ winder. The measurement station can be placed in a location to which the rolls are transferred next from the winder, for example at the location of the supporting base following the winding position, onto which base the roll is rolled from the top of the carrier drum and stopped.

FIG. 2 shows a first principle of the method according to the invention, in which a customer roll R wound around a core in the slitter winder is pressed from above by means of a press member 1 positioned at the end of a pivotal arm 2. The arm is arranged pivotable in the vertical plane, and it is attached to a suitable frame structure. The arm 2 is pressed down and at the same time the press member 1 is pressed against the roll R with a force device 3 arranged between the frame and the arm 2. The angular position of the pivotal arm 2 (angle θ) is measured by means of an angular sensor 4. By means of the angle and the force produced by the force device 3 it is possible to determine the depression of the press member 1 as a function of the radial force produced by the press member 1.

The force device 3 can be for example a hydraulic cylinder that produces a force that can be measured and on the basis of the same it is possible to calculate the force produced by the press member 1.

The press member 1 can be relatively small, but it is a prerequisite for its function that it does not change its form in the loading. The press member 1 can be made of steel or another suitably hard material. The lower surface of the press member is planar and the plane is positioned approximately tangentially with respect to the peripheral surface of the reel.

In order to be able to measure the actual loading force accurately, it is possible to utilize a suitable force sensor 5 on the lower surface of the press member 1. This force sensor measures directly the nip force effective in the nip between the surface of the force member 1 and the peripheral surface of the roll R. It is possible to use for example a pressure sensitive film sensor that is capable of giving a measurement signal proportional to the force. One example is a piezoresistive measurement film or a corresponding film sensor. By using a large surface film sensor or several sensors at different locations of the press member 1, it is also possible to measure the shape of the nip, i.e. the contact width, by means of which more information can be obtained. The contact width, i.e. the extent of the contact area in the direction of the periphery of the roll also indicates the deflection, wherein by means of a suitable sensor arrangement of the press member it is possible to measure both the force and the deflection.

Figure 3:
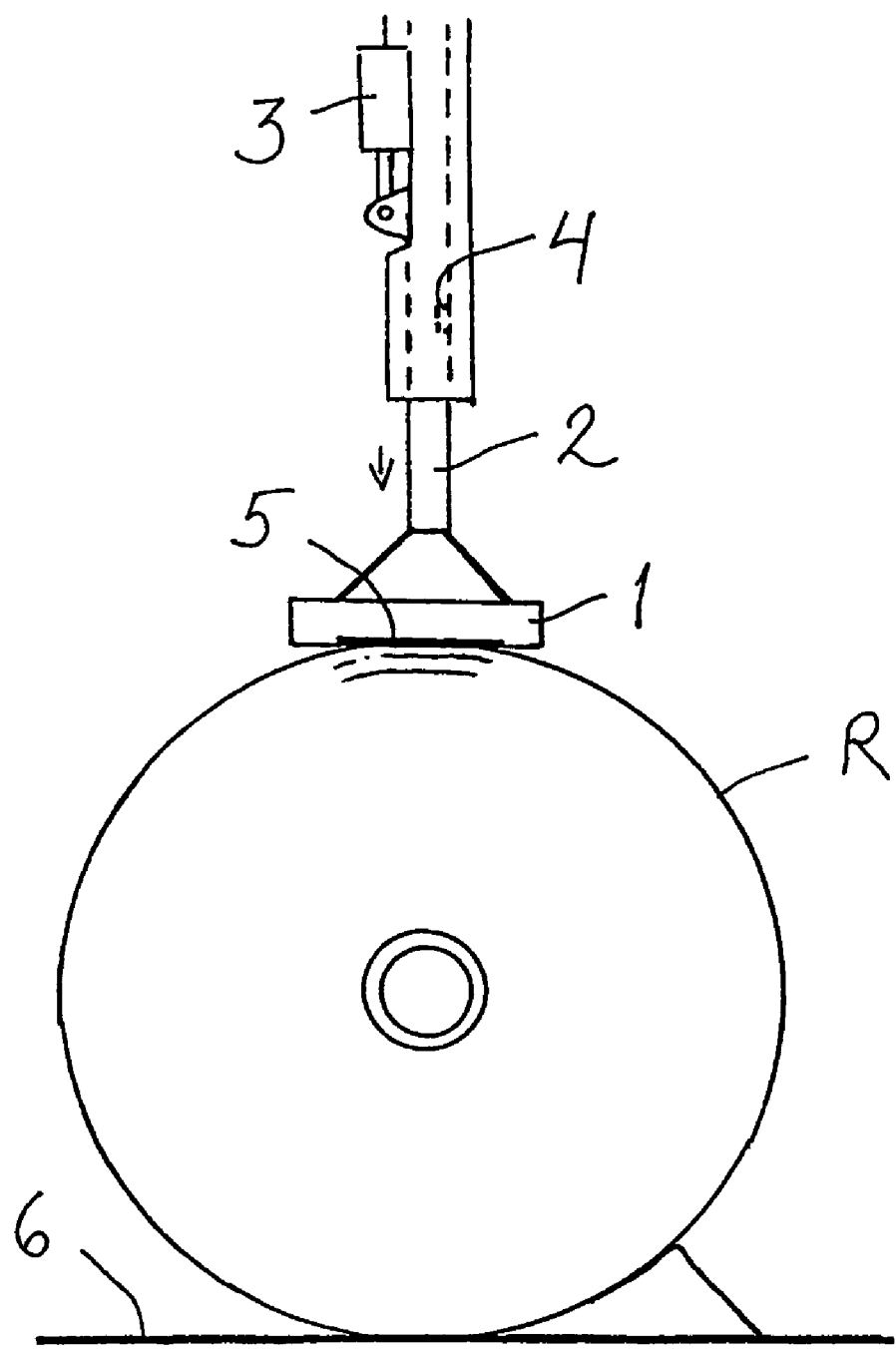

FIG. 3 shows another method in which a press member 1 is also positioned at the end of an arm 2. The function is analogous with FIG. 2, with the distinction that the force device 3 produces a linear movement, because the press member 1 and the arm 2 are arranged to move linearly in a guide. Also in this case it is possible to determine the force on the basis of the force used by the force device 3 or the force sensor 5 placed in the press member 1. To measure the movement proportional to the deflection, it is in this alternative possible to utilize a sufficiently accurate sensor 4 capable of measuring the linear movement. In this alternative it is also possible to determine the deflection by means of the sensor of the press member, if it can be utilized to determine the extent of the contact area.

In the measurement position of both FIG. 2 and 3, the roll R has been transferred away from the winding position. The measurement station comprises a measurement base 6 on which the roll is located sufficiently well supported from below, its rolling being prevented. The supporting base 6 can be located for example on the floor level. It is an advantage of performing the measurement outside the reel-up or winder that the measurement can be conducted without disturbing the reeling or winding process. When the measurement is conducted in a station in which the rolls are normally discharged when their winding is complete, the sequence of the set change of the winder will not be disturbed either. Since it is possible to wind a new roll in the winder at the same time when the roll R is measured in the measurement station, the winding process will not be disturbed and measurements can be conducted in principle until the roll must be transferred away from the path of the next roll coming from the winding process, said roll being the next one to be measured in the same measurement station.

Figure 4:
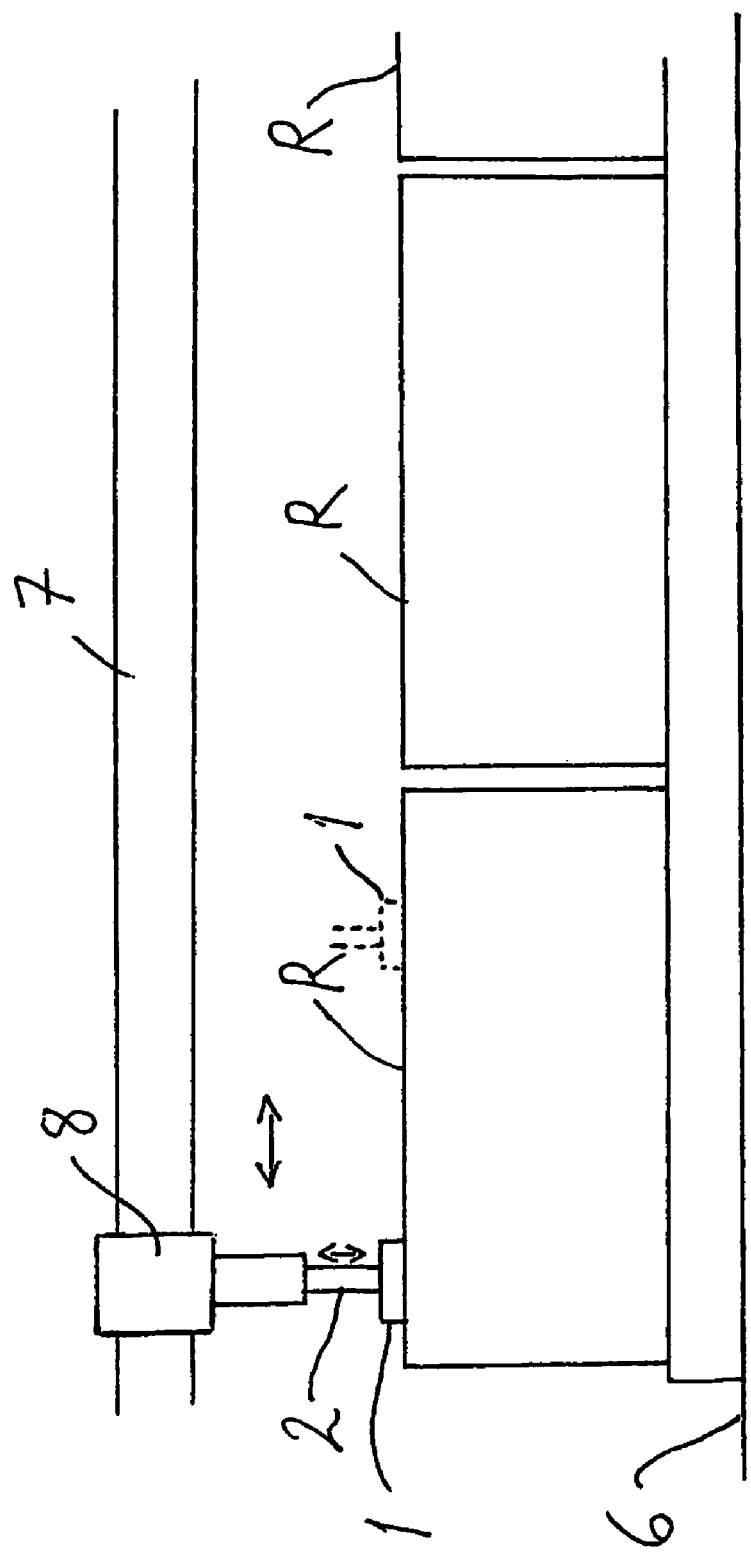
FIG. 4 shows a preferred embodiment of the method in a front view of the reel.

FIG. 4 shows yet another advantageous embodiment. The press member 1 is arranged to move in the cross direction, i.e. in the axial direction of the roll (longitudinal direction of the core), wherein it is possible to determine the force-deflection curve at different locations of the roll. The curves measured at different locations can be used for measuring the cross-directional profile of the radial module of the roll. In practice, the measurement station of FIG. 4 is implemented in such a manner that the press member 1 is arranged movable on a guide 7 extending in the cross direction, from which guide the arm 2 supporting the press member 1 can be suspended by fastening it for example to a carriage 8 or the like moving back and forth in the longitudinal direction of the guide.

The arrangement of FIG. 4 can also be utilized for measuring several adjacent rolls, which situation occurs when several rolls wound from the same web after the slitting operation is taken out of the reel-winder. The press member 1 is transferred successively on top of each reel. On each roll, it is possible to measure one point or several points to determine a profile.

The above-mentioned examples of the embodiments do not restrict the invention. The method according to the invention can also be applied in continuously operating reel-ups that are arranged to reel a paper web of production width on consecutive machine reels. Such a measurement can be conducted for example when the machine reel is located outside the reeling position on reeling rails, or when the machine reel is positioned in the unwinder, before its unwinding begins. It is also possible to determine a profile for the machine reel. The main idea in this invention is that the measurements of force and deflection necessary in the calculation of the radial modulus of elasticity of paper or a corresponding material can be performed directly on a reel without disturbing the reeling or winding process, and thus the laboratory measurement stage that causes extra work can be omitted.

What is claimed is:

1. A method for determining a radial modulus of elasticity of a paper web or a corresponding web-like material, which can be reeled or wound on a reel, in which method the connection between the force and deflection of a web material arranged in layers is measured, wherein the method comprises the steps of:
   reeling or winding the web material to form a reel in a reeling or winding position, the reel defining a reel axis and a radial direction toward the reel axis;
   transferring the reel from the reeling or winding position to a measurement position; and
   making measurements of force and deflection so as to allow calculating the radial modulus of elasticity of the reel of the web material in the measurement position outside the reeling or winding position;
   wherein the reel of web material is loaded with a force in the radial direction which is predetermined, and deflection of the reel in the radial direction that corresponds to the force is measured and registered; and
   wherein while the reel of web material is being loaded with the predetermined force, a curve is obtained of the deflection of the reel in the radial direction as a function of the force.

2. The method of claim 1, wherein the curve obtained is compared to a theoretically calculated curve of deflection of the reel in the radial direction as a function of the force.

3. The method of claim 2, wherein when the theoretically calculated curve of deflection of the reel in the radial direction as a function of the force corresponds to the curve obtained from the measurement results, the radial modulus of elasticity is estimated from elastic parameters that have been used in calculating the theoretically calculated curve of deflection.

4. A method for determining a radial modulus of elasticity of a paper web or a corresponding web-like material, which can be reeled or wound on a reel, in which method the connection between the force and deflection of a web material arranged in layers is measured, wherein the method comprises the steps of:
   reeling or winding the web material to form a reel in a reeling or winding position, the reel defining a reel axis and a radial direction toward the reel axis;
   transferring the reel from the reeling or winding position to a measurement position; and
   making measurements of force and deflection so as to allow calculating the radial modulus of elasticity of the reel of the web material in the measurement position outside the reeling or winding position;
   wherein the reel of web material is loaded with a force in the radial direction which is predetermined, and deflection of the reel in the radial direction that corresponds to the force is measured and registered;
   wherein the reel is loaded with a planar surface of a press member moving in the radial direction toward the reel axis; and
   wherein the force is measured by a force sensor positioned in the press member loading the reel and the force sensor being in contact with the reel.

5. The method of claim 4, wherein the force sensor is also utilized to determine a loaded area extent on the reel.

6. The method of claim 5, wherein the deflection of the reel in the radial direction is determined on the basis of the loaded area extent on the reel.

7. A method for determining a radial modulus of elasticity of a paper web or a corresponding web-like material, which can be reeled or wound on a reel, in which method the connection between the force and deflection of a web material arranged in layers is measured, wherein the method comprises the steps of:

reeling or winding the web material to form a reel in a reeling or winding position, the reel defining a reel axis and a radial direction toward the reel axis;

transferring the reel from the reeling or winding position to a measurement position; and making measurements of force and deflection so as to allow calculating the radial modulus of elasticity of the reel of the web material in the measurement position outside the reeling or winding position;

wherein the reel of web material is loaded with a force in the radial direction which is predetermined, and deflection of the reel in the radial direction that corresponds to the force is measured and registered; and wherein the force is measured by a force sensor positioned in a press member loading the reel and the force sensor being in contact with the reel.

8. The method of claim 7, wherein the force sensor is also utilized to determine a loaded area extent on the reel.

9. A method for determining a radial modulus of elasticity of a paper web or a corresponding web-like material, which can be reeled or wound on a reel, in which method the connection between the force and deflection of a web material arranged in layers is measured, wherein the method comprises the steps of:

reeling or winding the web material to form a reel in a reeling or winding position, the reel defining a reel axis and a radial direction toward the reel axis;

transferring the reel from the reeling or winding position to a measurement position; and making measurements of force and deflection so as to allow calculating the radial modulus of elasticity of the reel of the web material in the measurement position outside the reeling or winding position; and wherein a profile of the radial modulus of elasticity of the web material is determined by performing a force and a deflection measurement at different points in the axial direction of the reel.

10. The method of claim 9, wherein the profile is measured by moving a press member in an axial direction of the reel and performing the force and the deflection measurements at the different points with the press member.

11. A method for determining a radial modulus of elasticity of a paper web or a corresponding web-like material, which can be reeled or wound on a reel, in which method the connection between the force and deflection of a web material arranged in layers is measured, wherein the method comprises the steps of:

reeling or winding the web material to form a reel in a reeling or winding position, the reel defining a reel axis and a radial direction toward the reel axis;

transferring the reel from the reeling or winding position to a measurement position; and making measurements of force and deflection so as to allow calculating the radial modulus of elasticity of the reel of the web material in the measurement position outside the reeling or winding position; and wherein the radial modulus of elasticity of the web material is determined by performing a force and a deflection measurement on different adjacent reels by transferring a press member successively on top of said adjacent reels.

12. A method for determining a radial modulus of elasticity of a paper web that can be reeled or wound on a reel, in which method the connection between the force and deflection of the paper web arranged in layers in the reel is measured, wherein the method comprises the steps of:

reeling or winding the paper web to form a reel in a reeling or winding position, the reel defining a reel axis and a radial direction toward the reel axis;

transferring the reel from the reeling or winding position to a measurement position; and making measurements of force and deflection so as to allow and calculating the radial modulus of elasticity of the reel of the paper web in the measurement position outside the reeling or winding position; and wherein a profile of the radial modulus of elasticity of the paper web is determined by performing a force and a deflection measurement at different points in the axial direction of the reel.

13. The method of claim 12, wherein the profile is measured by moving a press member in an axial direction of the reel and performing the force and the deflection measurements at the different points with the press member.

14. A method for determining a radial modulus of elasticity of a paper web that can be reeled or wound on a reel, in which method the connection between the force and deflection of the paper web arranged in layers in the reel is measured, wherein the method comprises the steps of:

reeling or winding the paper web to form a reel in a reeling or winding position, the reel defining a reel axis and a radial direction toward the reel axis;

transferring the reel from the reeling or winding position to a measurement position; and making measurements of force and deflection so as to allow calculating the radial modulus of elasticity of the reel of the paper web in the measurement position outside the reeling or winding position, wherein the radial modulus of elasticity of the paper web is determined by performing a force and a deflection measurement on different adjacent reels by transferring a press member successively on top of said adjacent reels.

* * * * *